United States Patent [19]

Seymour

[11] Patent Number: 5,376,337
[45] Date of Patent: Dec. 27, 1994

[54] SALIVA SAMPLING DEVICE AND SAMPLE ADEQUACY SYSTEM

[76] Inventor: Eugene H. Seymour, 1465 Monaco Dr., Pacific Palisades, Calif. 90272

[21] Appl. No.: 94,407

[22] Filed: Jul. 19, 1993

Related U.S. Application Data

[63] Continuation-in-part of Ser. No. 47,713, Apr. 14, 1993, which is a continuation-in-part of Ser. No. 889,283, Jun. 3, 1992, which is a continuation-in-part of Ser. No. 857,574, Mar. 24, 1992, abandoned, which is a continuation-in-part of Ser. No. 838,609, Feb. 19, 1992, Pat. No. 5,268,148, which is a continuation-in-part of Ser. No. 831,776, Feb. 5, 1992, Pat. No. 5,260,031, which is a continuation-in-part of Ser. No. 775,195, Oct. 11, 1991, Pat. No. 5,283,038, and a continuation-in-part of Ser. No. 722,333, Jun. 25, 1991, abandoned, and a continuation-in-part of Ser. No. 629,278, Dec. 18, 1990, abandoned.

[51] Int. Cl.⁵ .................. C12M 1/28; G01N 33/487
[52] U.S. Cl. .................... 422/101; 128/760; 422/58; 422/99; 435/294; 435/295
[58] Field of Search .......... 128/732, 760, 762, 769; 422/58, 99–102; 435/294–295; 436/501, 514, 518, 524, 525, 528, 530, 531

[56] References Cited

U.S. PATENT DOCUMENTS

| | | | |
|---|---|---|---|
| 3,620,677 | 11/1971 | Morison | 422/56 |
| 3,783,104 | 1/1974 | Henshilwood et al. | 435/295 |
| 3,832,141 | 8/1974 | Haldopoulos | 422/101 |
| 3,870,639 | 3/1975 | Moore et al. | 422/101 X |
| 3,966,558 | 6/1976 | Calva-Pellicer | 435/295 |
| 4,150,950 | 4/1979 | Takeguchi et al. | 422/102 |
| 4,175,439 | 11/1979 | Laker | 604/1 X |
| 4,210,623 | 7/1980 | Breno et al. | 422/101 |
| 4,444,193 | 4/1984 | Fogt et al. | 422/58 X |
| 4,624,929 | 11/1986 | Ullman | 422/100 X |
| 4,635,488 | 1/1987 | Kremer | 422/58 X |
| 4,895,808 | 1/1990 | Romer | 422/101 X |
| 4,897,193 | 1/1990 | Cais et al. | 422/101 X |
| 4,961,432 | 9/1990 | Guirguis | 128/760 |
| 4,973,450 | 11/1990 | Schlüter | 422/101 |
| 4,999,285 | 3/1991 | Stiso | 422/58 X |
| 5,084,245 | 1/1992 | Berke et al. | 422/101 X |
| 5,145,789 | 9/1992 | Corti et al. | 422/101 X |
| 5,250,412 | 10/1993 | Giegel | 435/295 X |
| 5,259,956 | 11/1993 | Mercer et al. | 422/101 X |
| 5,268,148 | 12/1993 | Seymour | 422/101 |

FOREIGN PATENT DOCUMENTS

63-293440  11/1988  Japan ................ 128/760

*Primary Examiner*—James C. Housel
*Assistant Examiner*—Arlen Soderquist
*Attorney, Agent, or Firm*—W. Edward Johansen

[57] ABSTRACT

A saliva testing device includes a sample container opened at one end, a tube, a piston, a holding reservoir and a filter. The piston is fixed to a first end of the tube on a first side of the piston and has a hole in fluid communication with the tube. The piston fits closely and slidably within the sample container. An absorbent pad is affixed to the piston on a second side thereof in fluid communication with the hole in the piston. The holding reservoir is in fluid communication with a second end of the tube. The filter is in fluid communication with a second end of the tube. The absorbent pad receives a sample of fluid to be tested. When the piston is slidably inserted into the sample container, a pressure is generated forcing the saliva of fluid into the holding reservoir through the tube.

1 Claim, 10 Drawing Sheets

SALIVA SAMPLING DEVICE AND SAMPLE ADEQUACY SYSTEM

This application is a continuation-in-part of the application filed Apr. 14, 1993 under Ser. No. 08/047,713; which is a continuation-in-part of the application filed Jun. 3, 1992 under Ser. No. 889,283; which is a continuation-in-part of the application filed Mar. 24, 1992 under Ser. No. 857,574, now abandoned; which is a continuation-in-part of the application filed Feb. 19, 1992 under Ser. No. 838,609, now U.S. Pat. No. 5,268,148; which is a continuation-in-part of the application filed Feb. 5, 1992 under Ser. No. 831,776, now U.S. Pat. No. 5,260,031; which is a continuation-in-part of all of the application filed Oct. 11, 1991 under Ser. No. 775,195, now U.S. Pat. No. 5,283,038, the application filed Jun. 25, 1991 under Ser. No. 722,333, now abandoned, and the application filed Dec. 18, 1990 under Ser. No. 629,278, now abandoned, the disclosures of which are incorporated herein by reference.

BACKGROUND OF THE INVENTION

The field of the invention is saliva sampling devices.

The current literature indicates saliva is used to conveniently, easily, safely and effectively test an individual for a variety of medical conditions. These tests for medical conditions include a hepatitis screening for restaurant employees, HIV, continue (nicotine) and cocaine screening by insurance companies and an HIV anti-body screening for medical purposes. Clinics for oncology, neurology, infertility, allergy, orthopedics and pain which had used urine, blood and serum samples to determine the medical conditions of their patients are now using samples of saliva for this same purpose.

U.S. Pat. No. 5,103,836 teaches a device for collecting immunoglobulins from the oral cavity for immunological testing. The device is a treated absorbent pad which is used to collect a specimen having a high concentration of immunoglobulins.

U.S. Pat. No. 4,150,950 teaches a sampling device which includes a container, a seal, a screw-cap, an elongated element and a specimen collector. The container has a liquid reagent which the seal seals into the bottom portion thereof capable of preserving the activity of a particular specimen. The specimen collector is attachable to the inside of the screw cap through the elongated element which is of sufficient length to immerse the specimen collector into the liquid. After a specimen has been obtained, the specimen collector, which is attached to the screw cap, is forced through the seal into the liquid preservative as the screw cap is fastened tightly onto the container.

SUMMARY OF INVENTION The present invention is generally directed to a saliva sampling device which includes a sample container and a sample collector. The sample collector includes an absorbent pad.

In a first separate aspect of the present invention, the sample collector has a tube and a piston which is fixed to a first end of the tube on a first side of the piston having a hole in fluid communication with the tube. The piston fits closely and slidably within the sample container. The absorbent pad is affixed to the piston on a second side thereof in fluid communication with the hole in the piston.

In a second separate aspect of the present invention, the saliva sampling device also includes a filter in fluid communication with a second end of the tube.

In a third separate aspect of the present invention, the saliva sampling device also includes a holding reservoir in fluid communication with a second end of the tube.

In a fourth separate aspect of the present invention, the saliva sampling device also includes a holding reservoir and a filter. The holding reservoir is in fluid communication with a second end of the tube. The filter is in fluid communication with the holding reservoir through the tube. The filter has gold conjugate disposed therein.

In a fifth separate aspect of the present invention, the saliva sampling device further includes a layer of absorbent material and a membrane with a dot testing material. The layer of absorbent material is disposed in the holding reservoir in fluid communication with the filter. The membrane is disposed in the holding reservoir in fluid communication with the holding reservoir.

In a sixth separate aspect of the present invention, the absorbent pad has a first portion, a second portion and a third portion. The first portion is exposed. The second portion is disposed within the piston and is enclosed thereby. The third portion is disposed in the tube. An indicator activated by a sample of saliva is disposed in the third portion.

In a seventh separate aspect of the present invention, the absorbent pad has a first portion, a second portion and a third portion. The first portion is exposed. The second portion is disposed within the piston and is enclosed thereby. The third portion is disposed in the tube. A drop of testing material for detecting the presence of analyte within a sample of saliva is disposed in the third portion.

Other aspects and many of the attendant advantages will be more readily appreciated as the same becomes better understood by reference to the following detailed description and considered in connection with the accompanying drawing in which like reference symbols designate like parts throughout the figures.

The features of the present invention which are believed to be novel are set forth with particularity in the appended claims.

DESCRIPTION OF THE PREFERRED EMBODIMENT

Figure 1:
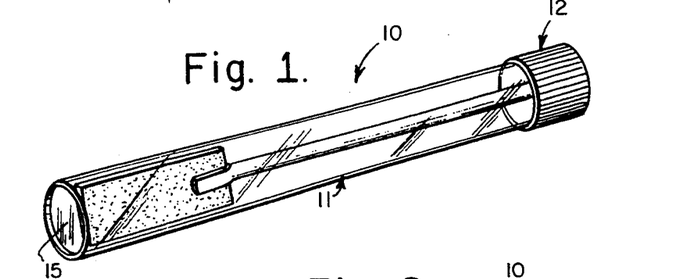
FIG. 1 is a perspective view of a saliva sampling device which includes a sample container and a saliva collector including a holder, an elongated member and a piece of filter paper.
Figure 2:
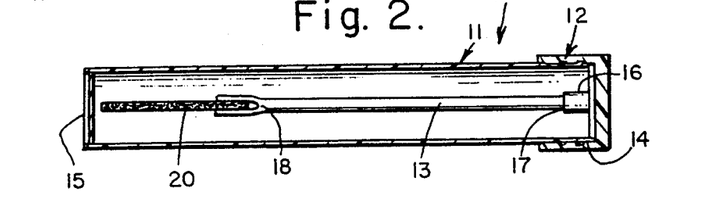
FIG. 2 is a side elevational view in cross-section of the saliva sampling device of FIG. 1.

Referring to FIG. 1 in conjunction with FIG. 2, a saliva sampling device 10 is used for collecting a measured sample of saliva. The saliva sampling device 10 includes a sample container 11, a cap 12 and a saliva collector 13, which is an elongated member. The sample container 11 has an open threaded end 14 and a closed end 15. The cap 12 has an inner surface 16 and is adapted to be mechanically coupled to the open threaded end 14 of the sample container 11 so that the cap 12 seals the sample container 11 air-tight. The saliva collector 13 has a first end 17 and a second end 18 with the first end 17 of which being mechanically coupled to the inner surface 16 of the cap 12. The saliva sampling device 10 also includes a piece of filter paper 20 which is of predetermined dimensions and which is mechanically coupled to the second end 18 of the saliva collector 13, so that a technician can collect a sample of saliva without touching the sample. Each sample of saliva is being collected wet and during the initial stages of testing of the saliva sampling device 10 a corresponding sample of blood serum is being compared thereto.

Figure 3:
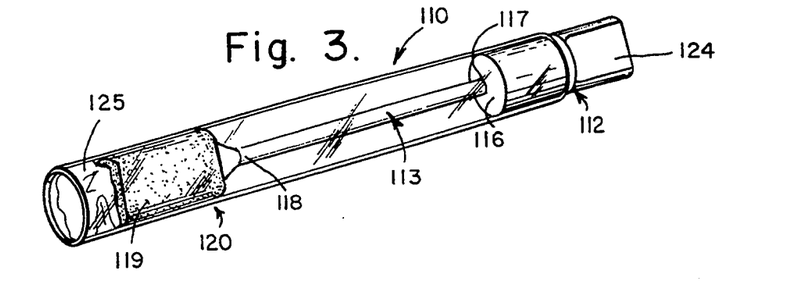
FIG. 3 is a perspective view of a saliva sampling device which includes a sample container and a saliva collector including a holder, a elongated member and a piece of filter paper.
Figure 4:
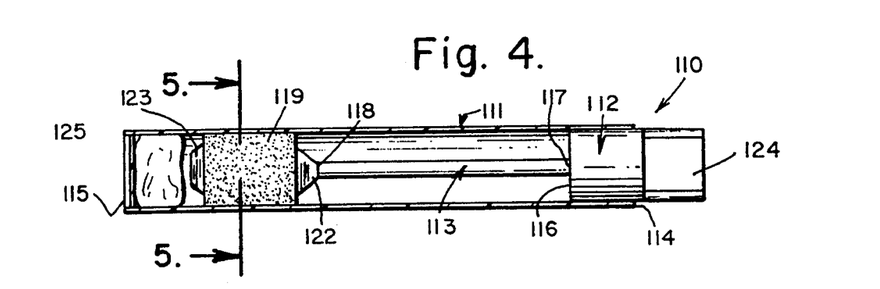
FIG. 4 is a side elevational view in cross-section of the saliva sampling device of FIG. 3.

Referring to FIG. 3 in conjunction with FIG. 4 a saliva sampling device 110 is used for collecting a measured sample of saliva. The saliva sampling device 110 includes a sample container 111, a plug 112 and a saliva collector 113, which is an elongated member. The sample container 111 has an open end 114 and a closed end 115. The plug 112 has an inner surface 116 and is adapted to be slidably coupled to the open end 114 of the sample container 111. The plug 112 seals the container 111 air-tight. The saliva collector 113 has a first end 117 and a second end 118. The first end 117 of the saliva collector 113 is mechanically coupled to the inner surface 116 of the plug 112.

Figure 5:
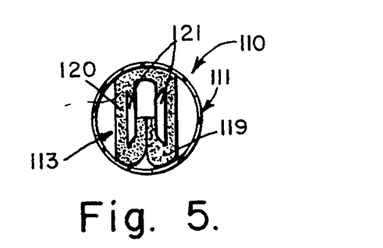
FIG. 5 is an end view in cross-section of the saliva sampling device of FIG. 3 taken along line 5—5 of FIG. 4.
Figure 6:
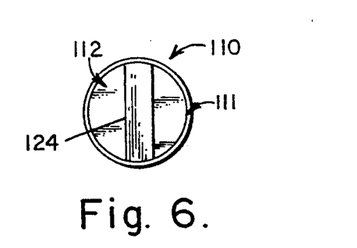
FIG. 6 is a top plan view of the saliva sampling device of FIG. 3.

Referring to FIG. 3 in conjunction with FIG. 4 and FIG. 5 the saliva sampling device 110 also includes a piece of filter paper 119 of pre-determined dimensions and a rectangular paddle assembly 120. The rectangular paddle assembly 120 includes two parallel and contiguous flat plates 121 each of which has a first end 122 and a second end 123 and which are joined together at their first ends 122 and mechanically coupled to the second end 118 of the saliva collector 113. The piece of filter paper 119 is mechanically coupled to the rectangular paddle assembly 120 so that a technician can collect the measured sample of saliva without touching the sample. The saliva sampling device 110 further includes a labeling mechanism 124 and a dessican 125. The labeling mechanism 124 labels the sample container 111 with the name of the patient and the date when the measured sample of saliva was taken. The dessican 125 removes the moisture content from the collected sample of saliva. The saliva sampling device 110 may also include a mailer which is used to transport the collected sample of saliva to a clinical laboratory for processing and analysis.

Figure 7:
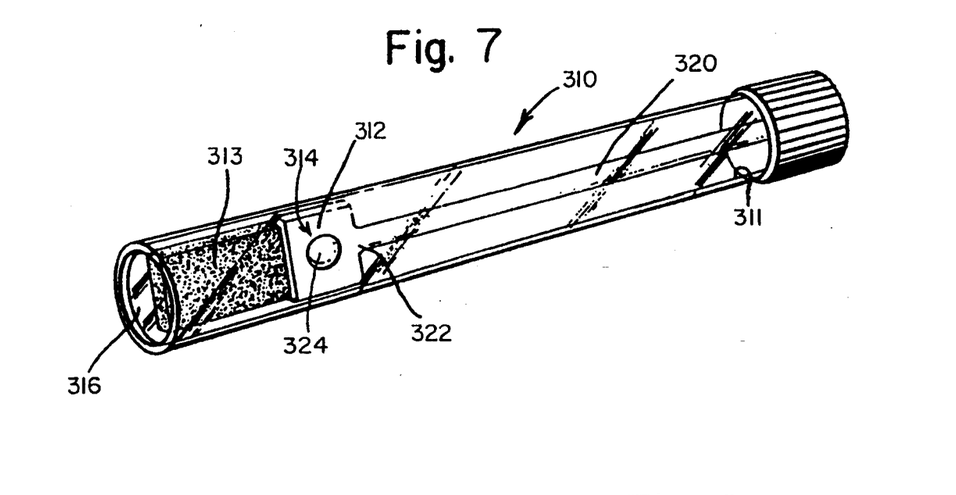
FIG. 7 is a perspective view of a saliva sampling device which includes a sample container, a saliva collector including a holder, a elongated member, a piece of filter paper and a sample adequacy system.
Figure 8:
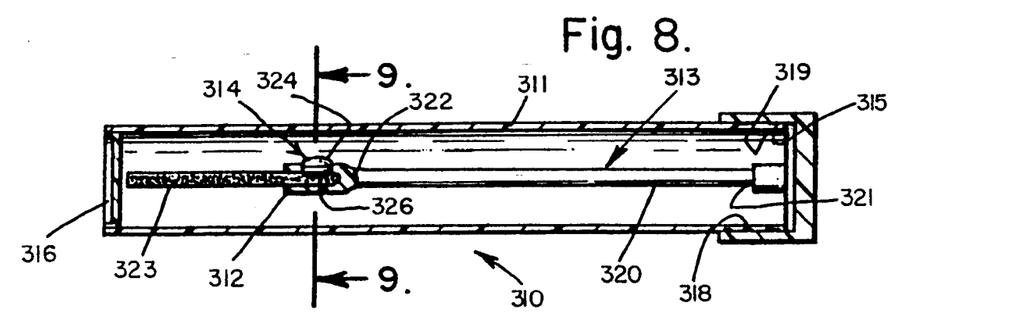
FIG. 8 is a longitudinal view in cross-section of the saliva sampling device of FIG. 7.

Referring to FIG. 7 in conjunction with FIG. 8 a saliva sampling device 310 includes a sample container 311, a holder 312, a saliva collector 313 and a sample adequacy system 314. The sample container 311 has an open threaded end 315 and a closed end 316. A solution 317 may be contained in the sample container 311. A cap 318 has an inner surface 319 and is coupled to the open threaded end 315 of the sample container 311 so that the cap 318 seals the sample container 311 air-tight. An elongated member 320 has a first end 321 and a second end 322. The first end 321 of the elongated member is coupled to the inner surface 319 of the cap 318. The holder 312 is coupled to the second end 322 of the elongated member 320. A piece of filter paper 323 is of predetermined dimensions and is mechanically coupled to the holder 312 so that a technician can collect a sample of saliva without touching the sample. The sample adequacy system 314 includes a plastic lens 324 and a hole 325 in the top surface of the holder 312 into which the plastic lens 324 is disposed. The top portion 326 of the piece of filter paper 323 is treated with a chemical reagent 327 which reacts with saliva by changing its color from a first color to a second color.

Figure 9:
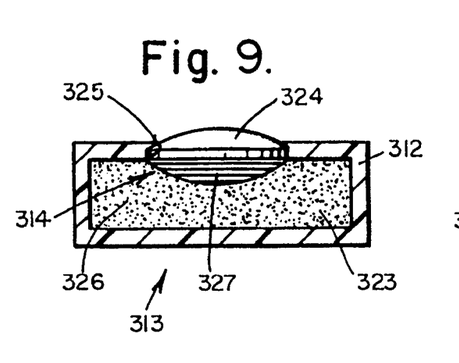
FIG. 9 is a cross-sectional view of the saliva collector of the saliva sampling device of FIG. 13 taken along line 9—9 of FIG. 8 showing the sample adequacy system before the saliva collector has been placed in a subject's mouth.
Figure 10:
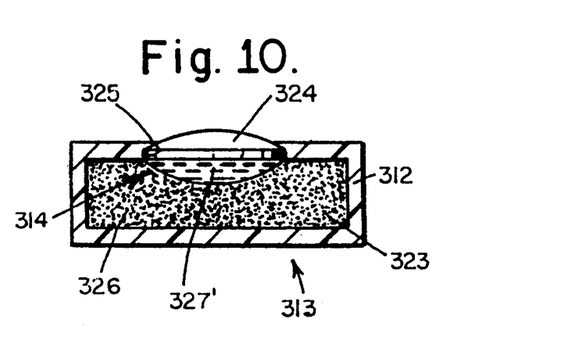
FIG. 10 is a cross-sectional view of the saliva collector of FIG. 7 taken along line 9—9 of FIG. 8 showing the sample adequacy system after the saliva collector has collected an adequate sample of saliva.

Referring to FIG. 7 in conjunction with FIG. 8, FIG. 9 and FIG. 10 before the saliva collector 313 has been placed in a subject's mouth the top portion 326 of the piece of filter paper 323 is of the color blue. When an adequate amount of saliva has been collected the saliva in the piece of filter paper 323 will reach the chemical reagent 327' and change the color blue to clear. Each sample of saliva will be collected wet and during the initial stages of testing of the saliva sampling device 310 a corresponding sample of blood serum is being compared thereto. Once an adequate amount of saliva has been collected the saliva the holder 312 and the piece of filter paper 320 are placed into the sample container 311 and shaken vigorously enough to separate the piece of filter paper 323 from the filter paper holder 319.

Figure 11:
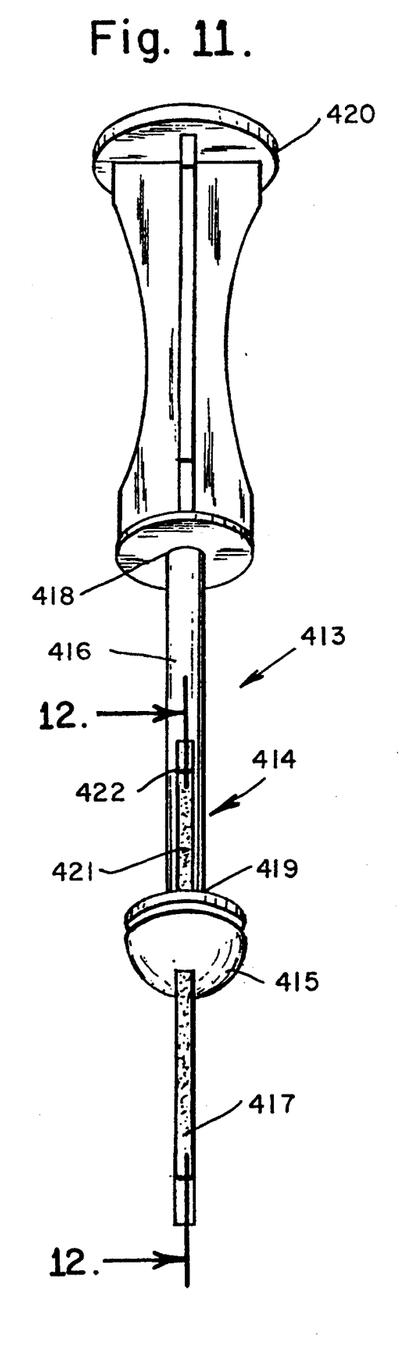
FIG. 11 is a perspective view of a sample collector.
Figure 12:
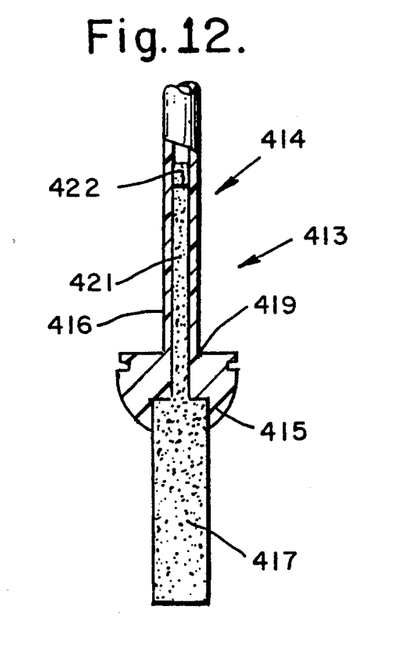
FIG. 12 is an elevational view in a partial cross-section of the sample adequacy system of the sample collector of FIG. 11 before it has collected a sample taken along line 12—12 of FIG. 11.
Figure 13:
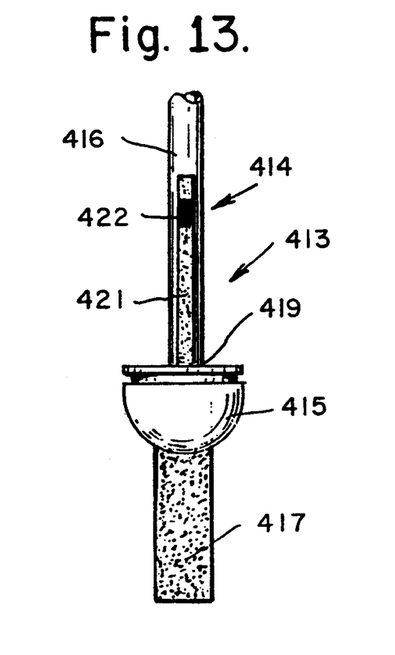
FIG. 13 is an elevational view of the sample adequacy system of FIG. 11 after the sample collector has collected an adequate sample.

Referring to FIG. 11 in conjunction with FIG. 12 and FIG. 13 a sampling device also includes a sample collector 413 with a sample adequacy system 414. The sample collector 413 includes a piston-shaped holder 415, an elongated member 416 and a piece of filter paper 417. The elongated member 416 has a first end 418 and a second end 419. The first end 418 of the elongated member 416 is coupled to a push tab 420. The piston-shaped holder 415 is coupled to the second end 419 of the elongated member 416. The piece of filter paper 417 is of predetermined dimensions and is mechanically coupled to the piston-shaped holder 415 so that a technician can collect a sample without touching it. The sample adequacy system 414 is formed by an extension 421 of the filter paper 417 and either a drop of dye 422 or a line of ink placed at the top of the extension 421 of the filter paper 417. When an adequate amount of sample has been collected the drop of dye 422 mixes with a small amount of the collected sample causing the drop of dye 422 to bleed into a larger area at the top of the extension 421 of the filter paper 417. The sample collector 413 selectively receives a sample. The sample collector 413 can be used to collect samples of bodily fluids. These bodily fluids include saliva, urine, water, tears and vaginal fluids. The components of the sampling device may be formed out of a plastic material which may be either opaque or non-opaque.

Figures 14, 16, 17:
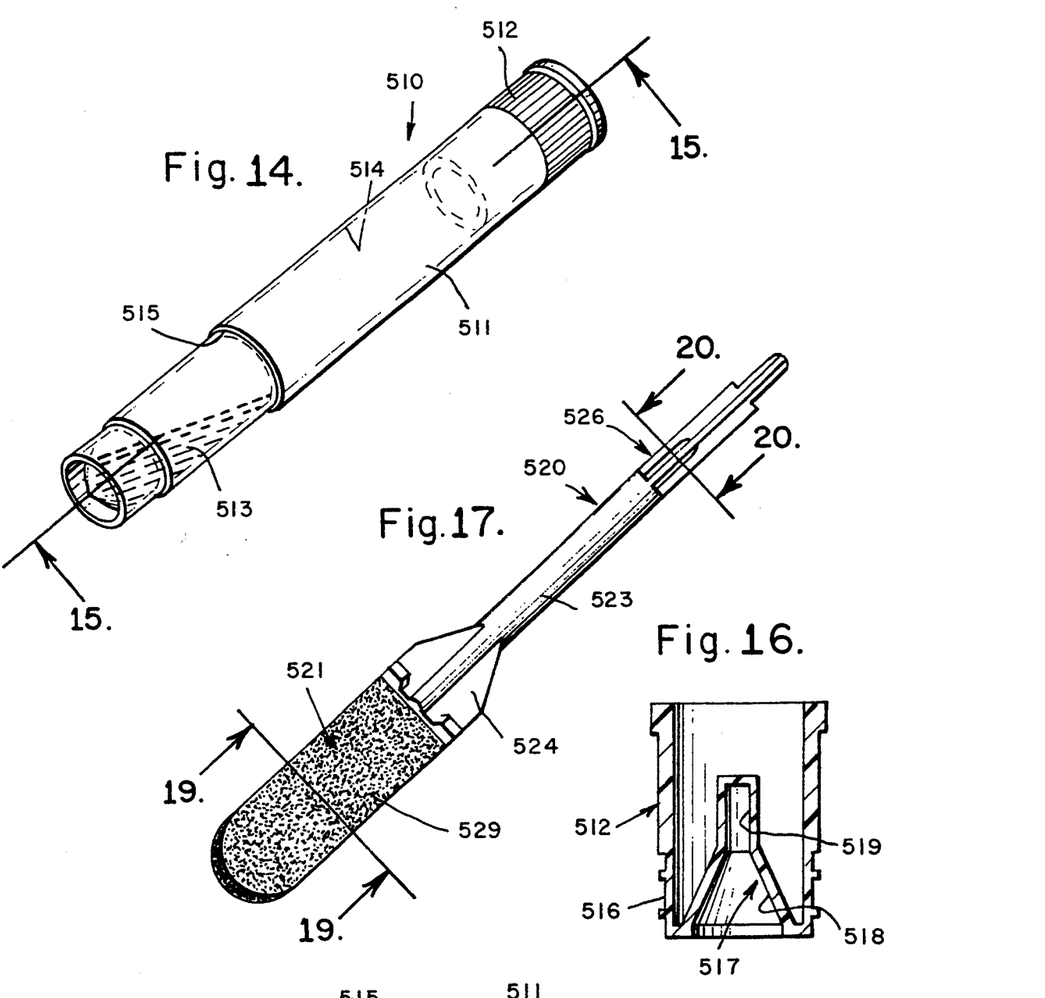
FIG. 14 is a perspective view of a saliva sampling device which includes a sample container and a cap.
FIG. 16 is a cross-sectional view of the cap of FIG. 14 taken along line 16—16 of FIG. 14.
FIG. 17 is a perspective view of a saliva collector of the saliva sampling device of FIG. 14 including a holder, a paddle and a piece of filter paper.
Figure 15:
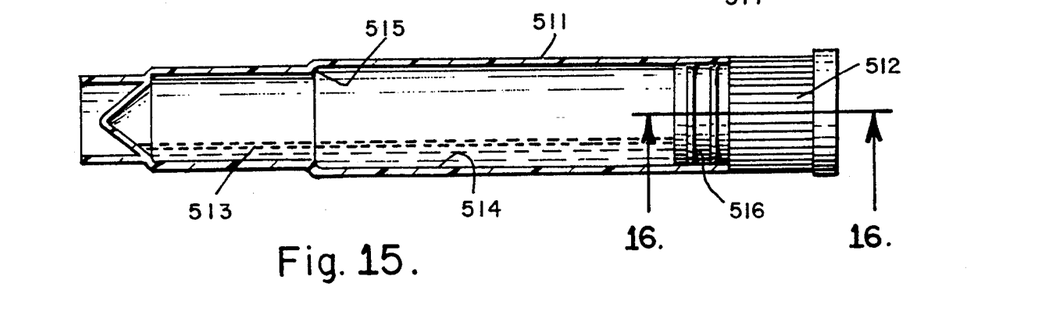
FIG. 15 is a cross-sectional view of the saliva sample container of FIG. 14 taken along line 15—15 of FIG. 14.

Referring to FIG. 14 in conjunction with FIG. 15 and FIG. 16 a saliva sampling device 510 includes a sample container 511, a cap 512 and a buffering solution 513. The sample container 511 has an inner wall surface 514 and a retaining ridge 515 which is disposed on the inner wall surface 514. The cap 512 has an outer wall surface 516 and an inner wall surface 517. The outer wall surface 516 of the cap 512 snugly engages the inner wall surface of the sample container. The inner wall surface 517 of the cap 512 has a truncated conical portion 518 having a top and a cylindrical portion 519 which is coupled to the truncated conical portion 518 adjacent to the top thereof.

Figure 18:
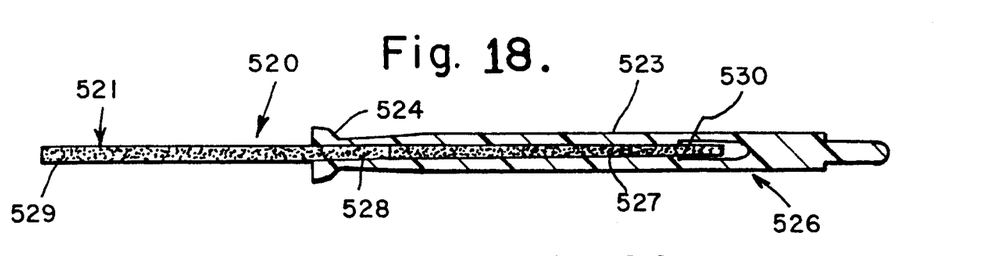
FIG. 18 is a longitudinal view in cross-section of the saliva collector of FIG. 17.
Figure 19:
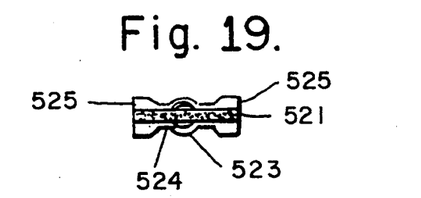
FIG. 19 is a transverse view in cross-section of the saliva collector of FIG. 17 taken along the line 19—19 of FIG. 17.

Referring to FIG. 17 in conjunction with FIG. 18 and FIG. 19 the saliva sampling device 510 also includes a sample collector 520 which has a piece 521 of filter paper and a holder 522 which has a tube 523 and a paddle 524 coupled to the piece 521 of filter paper. The paddle 524 has a peripheral edge 525 for engaging the retaining ridge 515 of the sample container 511.

Figure 20:
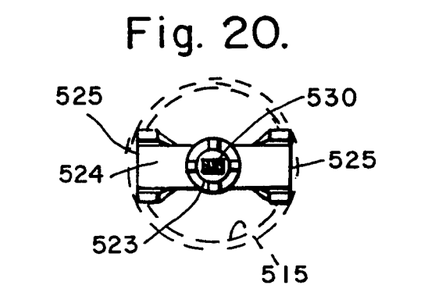
FIG. 20 is a transverse view in cross-section of the saliva collector of FIG. 17 taken along the line 20—20 of FIG. 17.

Referring to FIG. 17 in conjunction with FIG. 18 and FIG. 20 the saliva sampling device 510 further includes a sample adequacy system 526 having an indicator 527. The indicator is activated by a sample of saliva. The piece 521 of filter paper has a first portion 528, a second portion 529 and a third portion 530. The third portion 530 is disposed adjacent to the first portion 528. The first portion 528 is disposed within the paddle 524 enclosed thereby. The third portion is disposed in the tube 523 wherein the second portion 529 thereof is exposed. The indicator 527 is disposed in the third portion 530 so that the indicator 527 does not interfere with the collection of the sample of saliva. When the second portion 529 is inserted into a test subject's mouth saliva fluidly couples the second portion 529 to the indicator 527 through the first and third portions 528 and 530.

Figure 21:
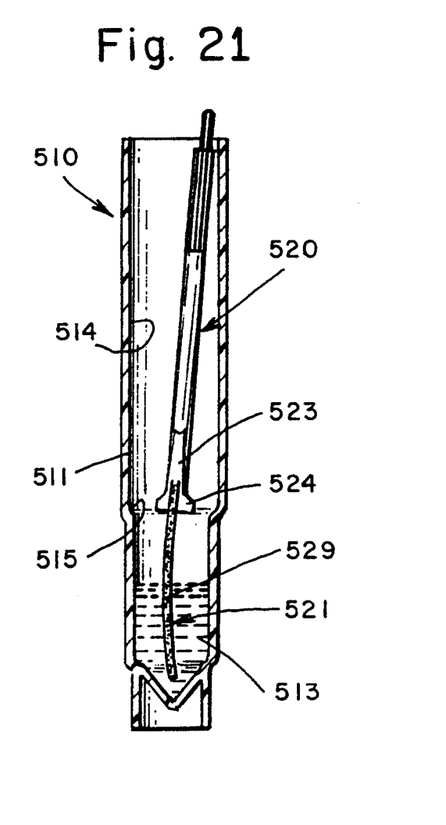
FIG. 21 is an elevational view in cross-section of the saliva sampling device of FIG. 14 without the cap thereof.
Figure 22:
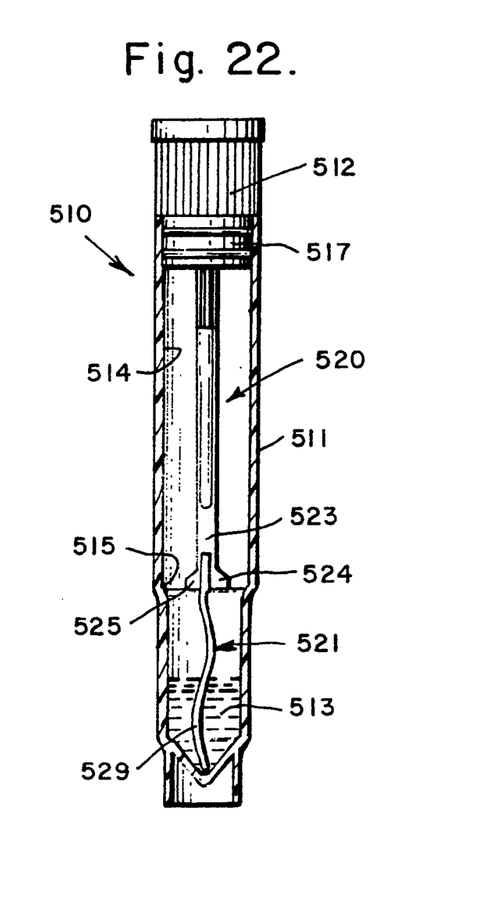
FIG. 22 is an elevational view in cross-section of the saliva sampling device of FIG. 14 with the cap thereof.

Referring to FIG. 21 in conjunction with FIG. 16, FIG. 17 and FIG. 22 when the sample collector 520 is placed in the sample container 511 the peripheral edge 525 of the paddle 524 engages the retaining ridge 515 of the sample container 511 so that the paddle 524 does not contact the buffering solution 513. When the truncated conical portion 518 of the cap 512 slidably engages the tube 523 the cylindrical portion 519 thereof snugly engages the tube 523.

Figures 23, 24:
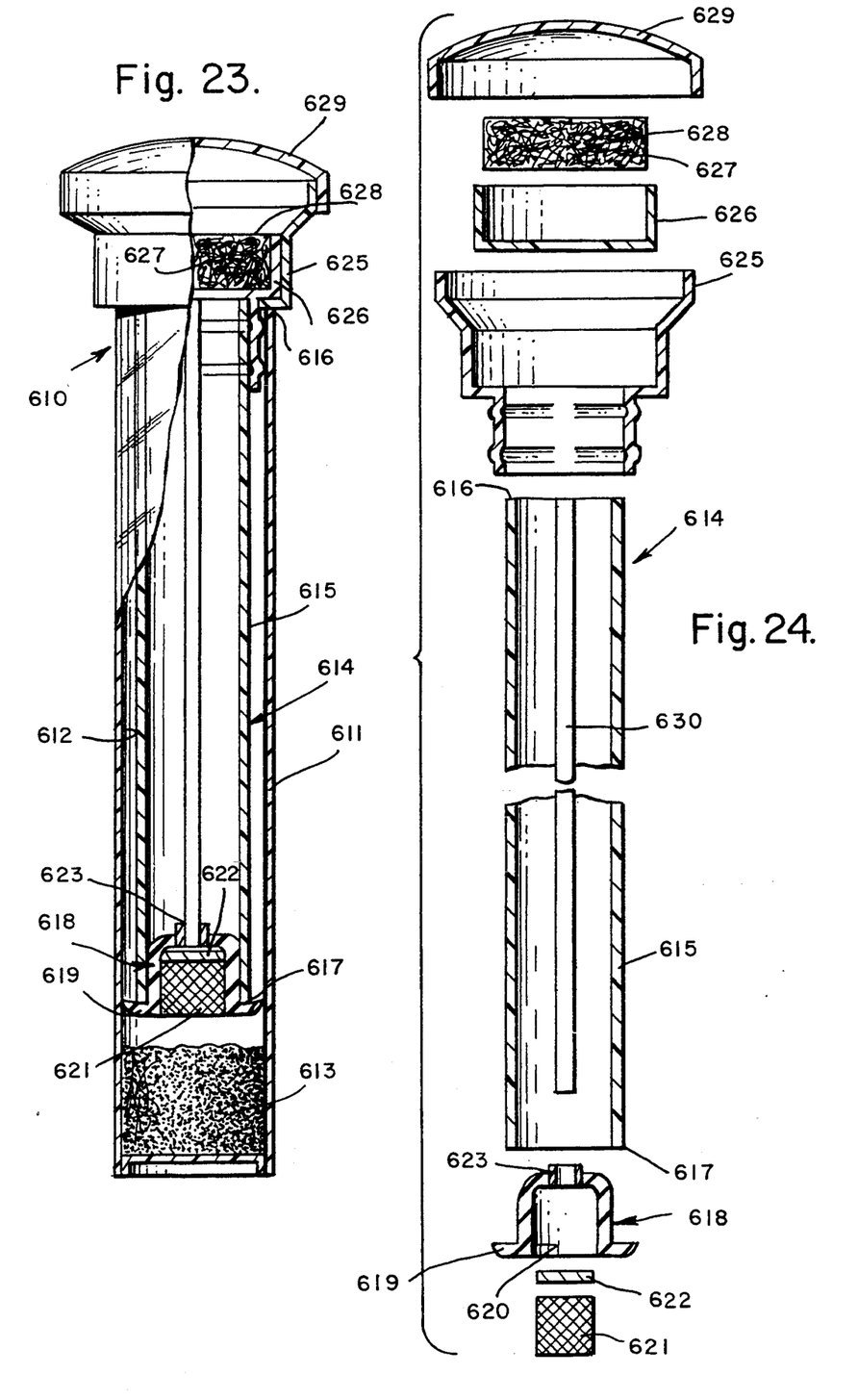
FIG. 23 is an elevational view in partial cross-section of the saliva testing device which has a separating device.
FIG. 24 is an exploded, elevational view in cross-section of the saliva testing device of FIG. 23.

Referring to FIG. 23 a saliva testing device 610 includes a sample container 611 having an inner wall surface 612, a piece 613 of filter paper and a separating device 614. The piece 613 of filter paper contains a saliva sample. The separating device 614 includes a hollow piston 615, which has a first open end 616 and a second open end 617, and a cylindrical, rubber gasket 618 which is snugly disposed in the second end 617. The cylindrical, rubber gasket 618 is slidably coupled to the sample container 611. The cylindrical, rubber gasket 618 has a flange 619, a first opening 620 into which a filter 621 and a conjugate disc 622 are placed and a second opening 623. The filter 621 and the first and second openings 620 and 623 are used in separating the saliva sample from the piece 613 of filter paper. The separating device 614 is used to press the saliva sample from the sample container 611 into the hollow piston 615. U.S. Pat. No. 4,895,808 teaches a test tube and tube-like adsorption column. The sample to be analyzed is prepared in solution and placed in the test tube. The tube-like adsorption column which has a seal and a valve member is forcefully fed into the test tube to force solutions through the valve member into the column and through a filter.

Referring to FIG. 24 in conjunction with FIG. 23 the saliva testing device 610 also includes a cap base 625, an absorbent shell 626, an absorbent mass 627, a membrane 628 and a cap window 629 and a wicking tube 630. The cap base 625 is snugly coupled to the sample container 611. The absorbent shell 626 is disposed in the cap base 625. The absorbent mass 627 is disposed in the absorbent shell 626. The membrane 628 covers the absorbent mass 627 and has been treated with a chemical agent. The cap window 629 is coupled to the cap base 625 and covers the membrane 628. The wicking tube 630 is fluid coupled to the absorbent shell 626. When the separating device 614 squeezes out the saliva sample into the hollow piston 615 the wicking tube 630 transports the saliva sample to the absorbent mass 627 through the absorbent shell 626 so that an analytical test of the saliva sample can be performed on the membrane 628. The results of the analytical test can be seen on the membrane 628 through the cap window 629.

Figure 25:
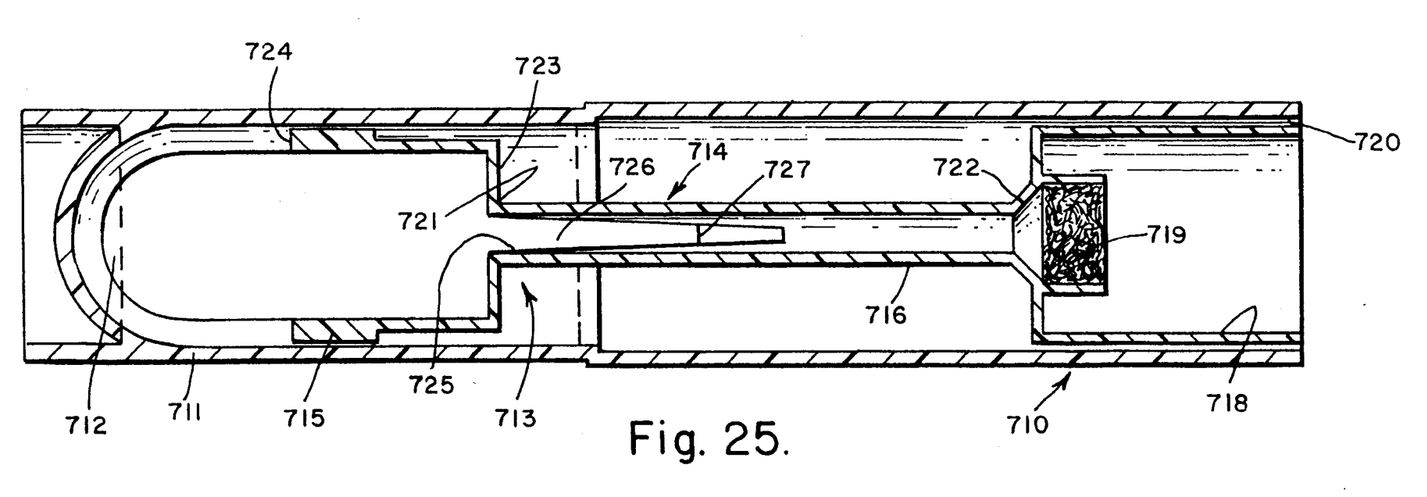
FIG. 25 is a front elevational view in cross-section of a saliva testing device having a sample collector.
Figure 26:
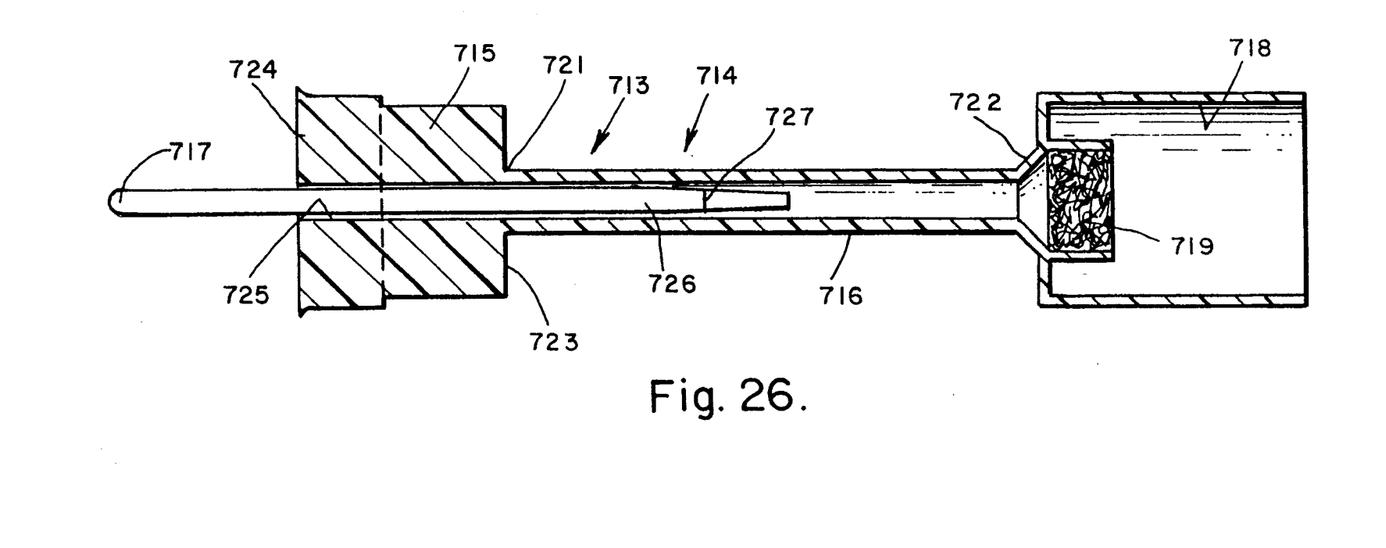
FIG. 26 is a side elevational view in cross-section of the sample collector of FIG. 25.

Referring to FIG. 25 in conjunction with FIG. 26 a saliva testing device 710 includes a sample container 711 containing a reagent fluid 712, a sample collector 713 with a sample adequacy system 714. The sample collector 713 can be used to collect samples of bodily and non-bodily fluids. These bodily and non-bodily fluids include, but are not limited to include, saliva, blood, serum, sweat, urine, water, tears, vaginal fluids, soil and oil. The components of the sampling device 710 may be formed out of a plastic material which may be either opaque or non-opaque. Unless indicated otherwise all of the components of the sampling device 710 are cylindrical.

Referring to FIG. 26 the sample collector 713 includes a piston 715, a tube 716, an absorbent pad 717, a holding reservoir 718 and a filter 719. The sample container 711 is open at one end 720. The tube 716 has a first end 721 and a second end 722. The piston 715 has a first side 723, a second side 724 and a hole 725. The piston 715 is fixed to the first end 721 of the tube 716 on the first side 723 of the piston. The hole 725 in the piston 715 is in fluid communication with the tube 716. The piston 715 fits closely and slidably within the sample container 711. The absorbent pad 717 is a flat, rectangular piece of filter paper and is affixed to the piston 715 on the second side 724 thereof in fluid communication with the hole 725 in the piston 715. The holding reservoir 718 is in fluid communication with the tube 716 at the second end 722 thereof. The filter 719 is in fluid communication with the tube 716 at the second end 722 thereof. The absorbent pad 717 receives a sample of fluid to be tested. The sample adequacy system 714 is formed by an extension 726 of the absorbent pad 717 and either a drop of dye 727 or a line of ink placed at the top of the extension 726 of the absorbent pad 717. When an adequate amount of sample has been collected the drop of dye 727 mixes with a small amount of the collected sample causing the drop of dye 727 to bleed into a larger area at the top of the extension 726 of the absorbent pad 717. When the piston 715 is slidably inserted into the sample container 711, the piston 715 generates a pressure thereby forcing the sample of fluid into the holding reservoir through the tube 716.

Figure 27:
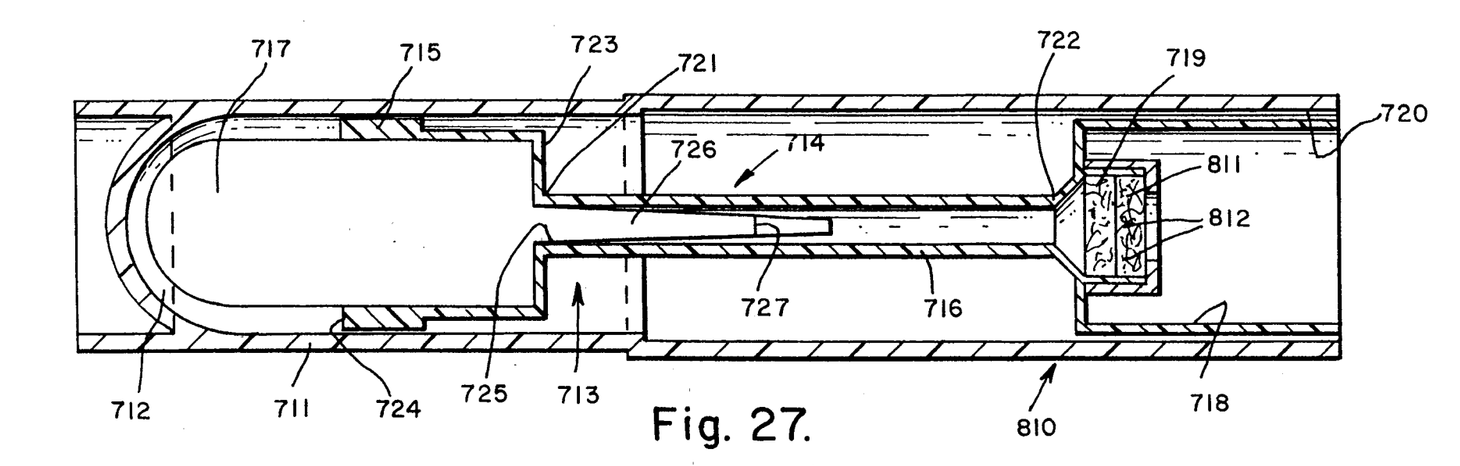
FIG. 27 is a front elevational view in cross-section of a saliva testing device.

Referring to FIG. 27 a saliva testing device 810 includes a sample container 711 containing a reagent fluid 712, a sample collector 713 with a sample adequacy system 714. The saliva testing device 810 also includes a membrane 811 which has gold 812 disposed therein. If the sample of fluid is being tested for the presence of an anti-body, then an antigen is conjugated with the gold 812; and if the sample of fluid is being tested for the presence of an antigen, then an anti-body is conjugated with the gold 812.

Figure 28:
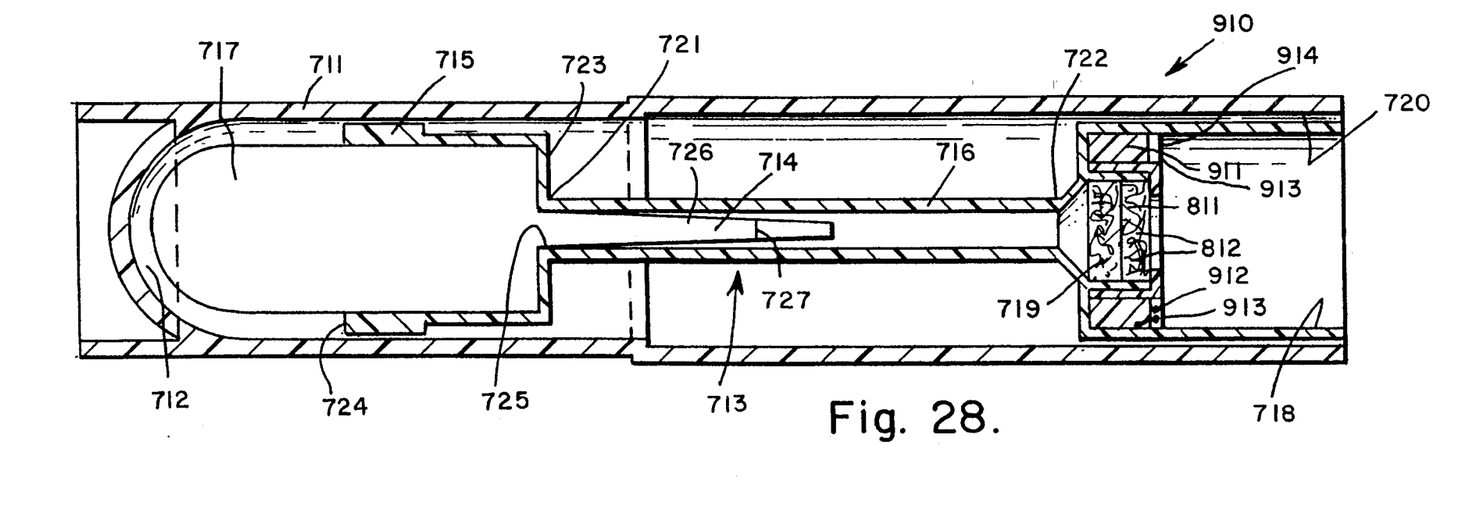
FIG. 28 is a front elevational view in cross-section of a saliva testing device

Referring to FIG. 28 a saliva testing device 910 includes a sample container 711 containing a reagent fluid 712, a sample collector 713 with a sample adequacy system 714. The saliva testing device 910 also includes a membrane 811 which has gold 812 disposed therein. If the sample of fluid is being tested for the presence of an anti-body, then an antigen is conjugated with the gold 812; and if the sample of fluid is being tested for the presence of an antigen, then an anti-body is conjugated with the gold 812. The saliva testing device 910 further includes a layer 911 of absorbent material and a test membrane 912. The layer 911 of absorbent material is doughnut-shaped and disposed in the holding reservoir 718 in fluid communication with the filter 811. The test membrane 912 is doughnut-shaped and disposed on the layer 911 of absorbent material in fluid communication with the membrane 811. The test membrane 912 has a test spot 913 of anti-anti-body and a control spot 914. When the sample of fluid passes over the test membrane 912, an analyte, either an antigen or an anti-body, if present, conjugates with the conjugated gold 812 and either the anti-body or the antigen, respectfully. When the conjugated gold 812, the antigen and the anti-body contacts the test spot 913 the anti-antibody conjugates with the conjugated gold 812, the antigen and the antibody thereby producing a color change. When a test is completed the control spot 914 indicates that the completed test is valid.

Figure 29:
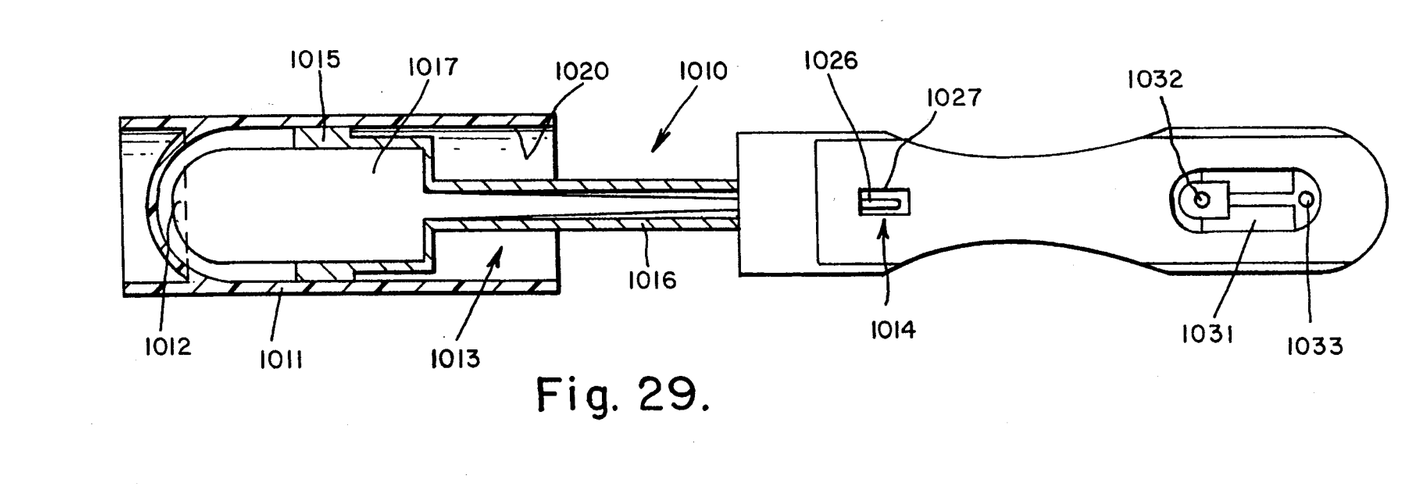
FIG. 29 is a front elevational view of a saliva testing device.
Figure 30:
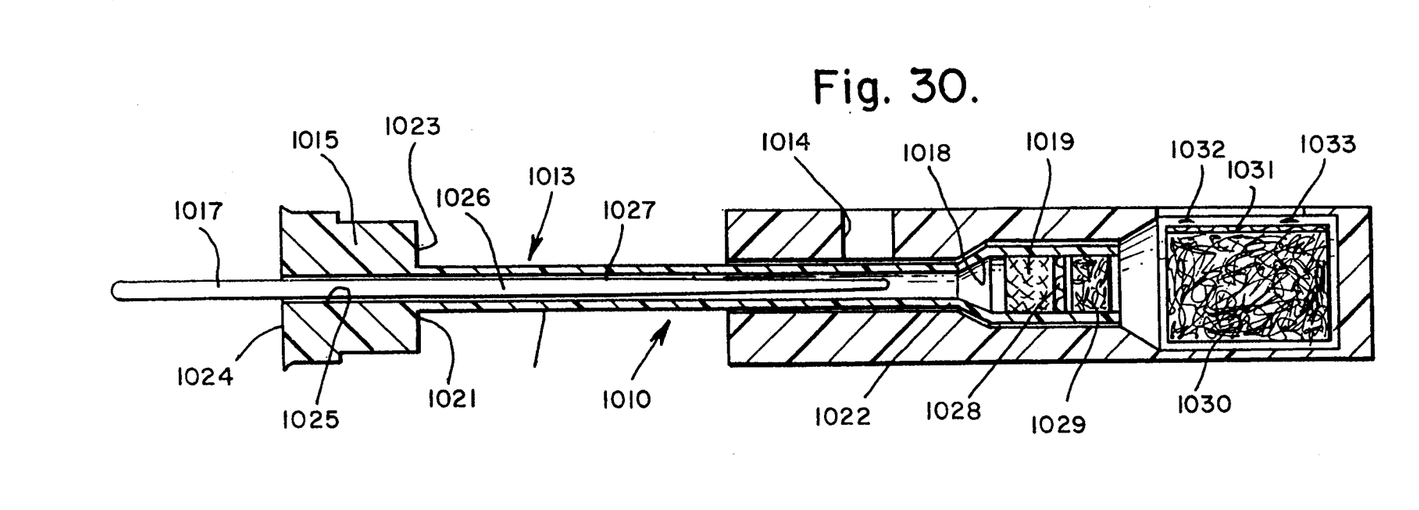
FIG. 30 is a side elevational view in cross-section of the saliva testing device of FIG. 31.

Referring to FIG. 29 in conjunction with FIG. 30 a saliva testing device 1010 includes a sample container 1011 containing a reagent fluid 1012, a sample collector 1013 with a sample adequacy system 1014. The sample collector 1013 can be used to collect samples of bodily and non-bodily fluids. These bodily and non-bodily fluids include, but are not limited to include, saliva, blood, serum, sweat, urine, water, tears, vaginal fluids, soil and oil.

Referring to FIG. 30 the sample collector 1013 includes a piston 1015, a tube 1016, an absorbent pad 1017, a holding reservoir 1018 and a first filter 1019. The sample container 1011 is open at one end 1012. The tube 1016 has a first end 1021 and a second end 1022. The piston 1015 has a first side 1023, a second side 1024 and a hole 1025. The piston 1015 is fixed to the first end 1021 of the tube 1016 on the first side 1023 of the piston. The hole 1025 in the piston 1015 is in fluid communication with the tube 1016. The piston 1015 fits closely and slidably within the sample container 1011. The absorbent pad 1017 is a flat, rectangular piece of filter paper and is affixed to the piston 1015 on the second side 1024 thereof in fluid communication with the hole 1025 in the piston 1015. The holding reservoir 1018 is in fluid communication with the tube 1016 at the second end 1022 thereof. The first filter 1019 is in fluid communication with the tube 1016 at the second end 1022 thereof. The absorbent pad 1017 receives a sample of fluid to be tested. The sample adequacy system 1014 is formed by an extension 1026 of the absorbent pad 1017 and either a drop of dye 1027 or a line of ink placed at the top of the extension 1026 of the absorbent pad 1017. When an adequate amount of sample has been collected the drop of dye 1027 mixes with a small amount of the collected sample causing the drop of dye 1027 to bleed into a larger area at the top of the extension 1026 of the absorbent pad 1017.

Still referring to FIG. 30 the sample collector 1013 also includes a membrane 1028, a second filter 1029, a roll 1030 of absorbent material, a test membrane 1031. The membrane 1028 which has gold 1032 disposed therein. When the piston 1015 is slidably inserted into the sample container 1011, the piston 1015 generates a pressure thereby forcing the sample of fluid into the tube 1016 so that the sample of fluid reaches the membrane 1028. If the sample of fluid is being tested for the presence of an anti-body, then an antigen is conjugated with the gold 1032; and if the sample of fluid is being tested for the presence of an antigen, then an anti-body is conjugated with the gold 1032. The test membrane 1031 has a test spot 1033 of anti-antibody. When the sample of fluid passes over the test membrane 1031, an analyte, either an antigen or an anti-body, if present, conjugates with the conjugated gold 1032 and either the anti-body or the antigen, respectfully. When the conjugated gold 1032, the antigen and the anti-body contacts the test spot 1033 the anti-antibody conjugates with the conjugated gold 1032, the antigen and the anti-body thereby producing a color change. The test membrane 1031 also has a control spot 1034. When a test is completed the control spot 1034 indicates that the completed test is valid.

Figure 31:
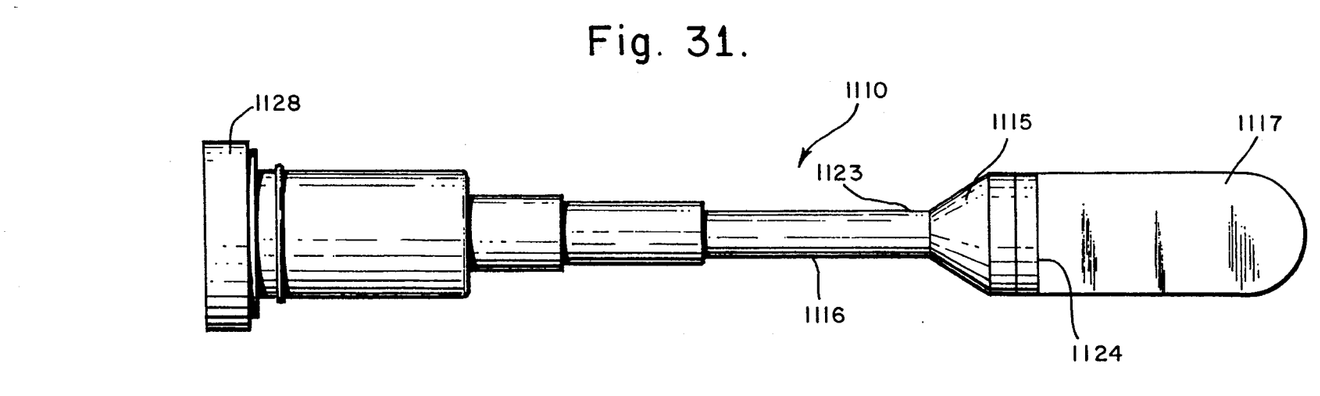
FIG. 31 is a front elevational view of a saliva testing device.
Figure 32:
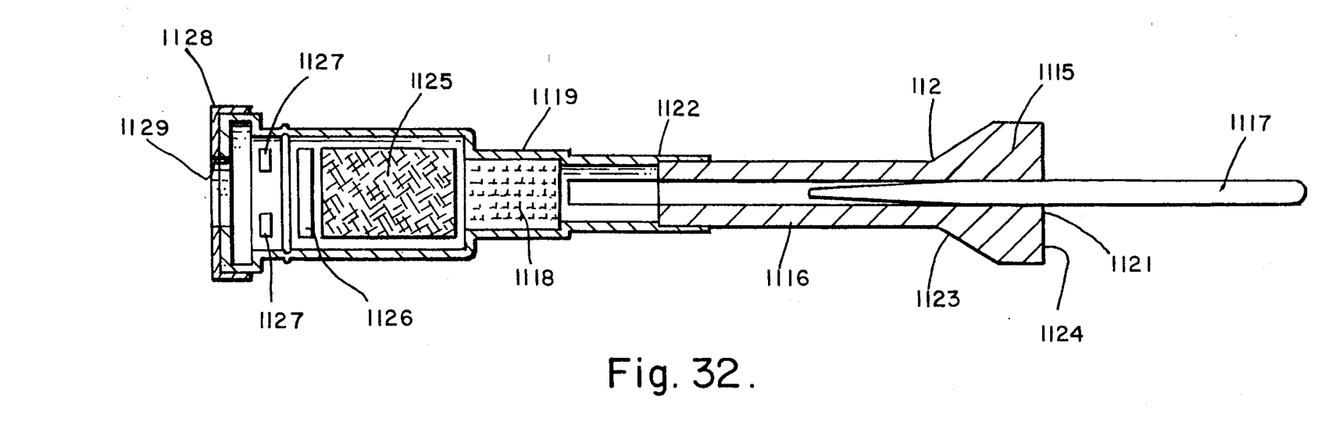
FIG. 32 is a side elevational view in cross-section of the saliva testing device of FIG. 31.

Referring to FIG. 31 in conjunction with FIG. 32 a saliva testing device 1110 includes a sample container containing a reagent fluid, a sample collector 1113 with a sample adequacy system. The sample collector 1113 can be used to collect samples of bodily and non-bodily fluids. These bodily and non-bodily fluids include, but are not limited to include, saliva, blood, serum, sweat, urine, water, tears, vaginal fluids, soil and oil. The components of the sampling device 1110 may be formed out of a plastic material which may be either opaque or non-opaque. Unless indicated otherwise all of the components of the sampling device 1110 are cylindrical.

Referring to FIG. 32 the sample collector 1113 includes a piston 1115, a tube 1116, an absorbent pad 1117, a holding reservoir 1118, a filter 1119 and a cap 1120. The sample container 1111 is open at one end 1112. The tube 1116 has a first end 1121 and a second end 1122. The piston 1115 has a first side 1123, a second side 1124 and a hole 1125. The piston 1115 is fixed to the first end 1121 of the tube 1116 on the first side 1123 of the piston. The hole 1125 in the piston 1115 is in fluid communication with the tube 1116. The piston 1115 fits closely and slidably within the sample container 1111. The absorbent pad 1117 is a flat, rectangular piece of filter paper and is affixed to the piston 1115 on the second side 1124 thereof in fluid communication with the hole 1125 in the piston 1115. The holding reservoir 1118 is in fluid communication with the tube 1116 at the second end 1122 thereof. The filter 1119 is in fluid communication with the tube 1116 at the second end 1122 thereof. The absorbent pad 1117 receives a sample of fluid to be tested. The sample adequacy system is formed by an extension of the absorbent pad 1117 and either a drop of dye or a line of ink placed at the top of the extension of the absorbent pad 1117. When an adequate amount of sample has been collected the drop of dye mixes with a small amount of the collected sample causing the drop of dye to bleed into a larger area at the top of the extension of the absorbent pad 1117.

Still referring to FIG. 32 the sample collector 1113 also includes a roll 1126 of absorbent material and a test membrane 1127. The 1119 which has gold 1128 disposed therein. When the piston 1115 is slidably inserted into the sample container, the piston 1115 generates a pressure thereby forcing the sample of fluid into the tube 1116 so that the sample of fluid reaches the test membrane 1127. If the sample of fluid is being tested for the presence of an anti-body, then an antigen is conjugated with the gold 1128; and if the sample of fluid is being tested for the presence of an antigen, then an anti-body is conjugated with the gold 1128. The test membrane 1127 has a test spot 1129 of anti-anti-body. When the sample of fluid passes over the test membrane 1127, an analyte, either an antigen or an anti-body, if present, conjugates with the conjugated gold 1128 and either the anti-body or the antigen, respectfully. When the conjugated gold 1032, the antigen and the anti-body contacts the test spot 1129 the anti-antibody conjugates with the conjugated gold 1128, the antigen and the anti-body thereby producing a color change. The test membrane 1127 also has a control spot 1130. When a test is completed the control spot 1130 indicates that the completed test is valid. The cap 1120 has a window 1131 through which the test spot 1129 and the control spot 1130 can be viewed.

From the foregoing it can be seen that a saliva sampling device has been described. It should be noted that the sketches are not drawn to scale and that distance of and between the figures are not to be considered significant.

Accordingly it is intended that the foregoing disclosure and showing made in the drawing shall be considered only as an illustration of the principle of the present invention.

What is claimed is:

1. A saliva testing device comprising:
   a. a sample container open at one end; and
   b. a sample collector including:
      i. a tube;
      ii. a piston fixed to a first end of said tube on a first side of said piston and including a hole in fluid communication with said tube, said piston fitting closely and slidably within said sample container;
      iii. an absorbent pad affixed to said piston on a second side thereof in fluid communication with said hole in said piston wherein said absorbent Dad has a first portion, a second portion and a third portion, said first portion being exposed, said second portion being disposed within said piston and being enclosed thereby, and said third portion being disposed in said tube;
      iv. a holding reservoir in fluid communication with said tube at a second end of said tube; and
      v. an indicator activated by a sample of saliva and disposed in said third portion so that said indicator does not interfere with the collection of said sample of saliva whereby when said first portion is inserted into a test subject's mouth saliva fluidly couples said first portion to said indicator in said third portion through said second portion.

* * * * *